United States Patent [19]

Pinto

[11] Patent Number: 4,592,364

[45] Date of Patent: Jun. 3, 1986

[54] APPARATUS FOR THE DIAGNOSIS OF HEART CONDITIONS

[76] Inventor: John G. Pinto, 9426 Black Hills Ct., San Diego, Calif. 92129

[21] Appl. No.: 608,798

[22] Filed: May 10, 1984

[51] Int. Cl.⁴ .............................................. A61B 5/02
[52] U.S. Cl. .................................. 128/672; 128/668; 128/695; 128/710
[58] Field of Search ................ 128/668, 672, 695, 710

[56] References Cited

U.S. PATENT DOCUMENTS 4,223,682  9/1980  Sherman ............................. 128/672

OTHER PUBLICATIONS

"Computer Automation of Blood-Pressure Measurements" Randall et al, IEEE Proceedings, vol. 63(10), 1399 (1975).

Primary Examiner—John Doll
Assistant Examiner—A. Pal
Attorney, Agent, or Firm—Charmasson & Holz

[57] ABSTRACT

An apparatus for analyzing the biomechanical behaviour of the cardiac muscle and for diagnosing pathological conditions of the heart. The apparatus measures and records the rise and fall of intra-ventricular pressure monitored by a transducer installed in a cardiac catheter or in an arterial probe. The pressure versus time recordings during both the systolic and diastolic phases are mathematically analyzed, and two parameters indicative of the biomechanical conditions of the muscle are derived. The parameters are then plotted against each other on a map in which diagnostic zones of various normal and pathological heart conditions are delineated.

12 Claims, 5 Drawing Figures

APPARATUS FOR THE DIAGNOSIS OF HEART CONDITIONS

FIELD OF THE INVENTION

This invention relates to medical apparatuses such as instruments used in the diagnosis of pathological disorders through recording and analysis of signals representing physiological activities. More specifically, the invention relates to instruments designed to analyze the behaviour of the cardiac muscle.

BACKGROUND OF THE INVENTION

In-vitro studies of muscular tissue and, in particular cardiac muscle bundles have been directed toward the understanding of the mechanical characteristics of the contracting phenomenon.

It was thought that once these characteristics had been defined, the mechanical behavior of a healthy organ could be represented in mathematical terms. Some of these terms could then be used as criteria in the diagnostic of pathological conditions.

The inventor focused his study on the analysis of the inotropy (from the Greek is, inos fiber; and tropos, behaviour) of the cardiac muscle, i.e. its contractibility.

Traditionally, the behaviour of the cardiac muscle has been analyzed by measuring the absolute values of the systolic and diastolic blood pressures and of the pulse rate; and by listening to auditory manifestations of the muscle valve activity. Electrocardiography provides only a gross inferential tool for the diagnosis of pathological heart conditions. Studies of time and displacement dependency in the behaviour of the cardiac organ have mainly been directed to the interpretation of force-versus-velocity curves, and the potential use of a theoretical maximum velocity parameter (obtained by converging extrapolations of a family of force-velocity curves) as an indicator of organ health. None of the previous time-dependence studies have suggested a practical interpretation of the consistent parameters around which this invention is implemented.

SUMMARY OF THE INVENTION

A simple phenomenological model of the contracting cardiac muscle has been developed which is capable of simulating most major mechanical attributes of the contraction phenomenon. From this model two critical parameters have been isolated. The first, y is indicative of the delayed time response of the cardiac muscle to the signal initializing contraction or relaxation. The second, x represents the inotropic state of the muscle, i.e. its ability to respond to the and the excitation and the particular mechano-chemical characteristic of that response.

These parameters can be derived from the continuous measurement of the intra-ventricular pressure during both the systolic and diastolic phases of the heart movement, according to the formula:

$$P(V,t) = B(V)t^y e^{-xt}$$

wherein P, is the intra-ventricular pressure as a function of the volume (V) and time (t); B represents the influence of the muscle length as a function of the volume (V) on the force of contraction; y is the excitation-contraction coupling parameter; and x is the inotropic coefficient.

It can be shown that the time Tmax necessary to reach peak pressure is equal to the ratio of y over x.

It is the principal object of the invention to provide an apparatus for analyzing the biomechanical behaviour of the cardiac muscle and for diagnosing its pathological conditions.

It is also an object of the invention to provide an apparatus for conducting clinical studies of the heart organ on live subjects, and in-vitro studies of muscular tissue samples.

A further object of the invention is to provide such an apparatus which calculates the y and x parameters for a particular muscle contracting phenomenon, and which uses them as criteria for the diagnosis of pathological conditions.

Another object of this invention is to provide a cardiac muscle analyzing apparatus which relies strictly on pressure-time dependency observations and uses only simple and reliable measurement of time and relative pressure variation.

These and other valuable objects are achieved by means of a simple monitoring device which records samples of intraventricular or arterial pressures during the systolic and diastolic phases of the heart movement; then, conducts a analytical study of the pressure-versus-time variations in order to extract the parameters characteristic of the muscle inotropy.

DESCRIPTION OF THE PREFERRED EMBODIMENT OF THE INVENTION

Figure 1:
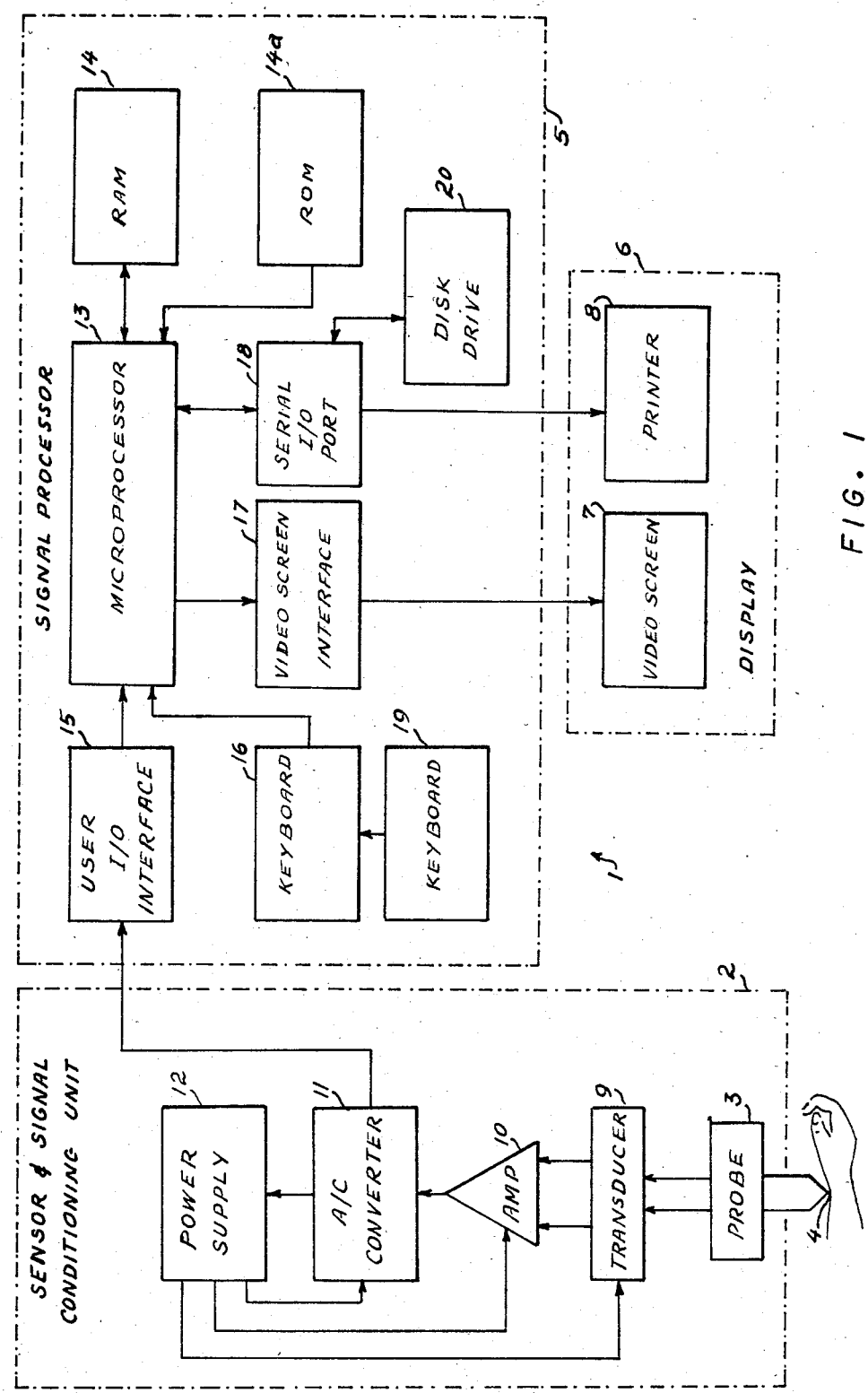
FIG. 1 is a general block diagram of a cardiac inotropy analyzing apparatus which constitutes the preferred embodiment of the invention.

Referring now to the drawing, there is shown in FIG. 1 a general block diagram of the cardiac inotropy analyzing apparatus 1 which is divided into three major components. The sensor and signal-conditioning unit 2 comprises a pressure monitoring probe 3 which is applied to the radial artery 4, or inserted into the heart by means of a catheter (not shown). The probe could be applied to any other convenient arterial location, depending upon the diagnosis sought. In a clinical environment the radial artery which is often punctured for other purposes would be most indicated. However, it is not absolutely necessary to penetrate the artery, and measurement may be taken by sensing the pressure of the arterial walls. The associated electronic circuit converts the monitored pressure into a digitally-coded signal which is fed to the second major component, the signal processor 5.

The signal processor analyzes the pressure signal and extracts the excitation-contraction coupling parameter y and the inotropic coefficient x from the time-response curve representing the pressure variation during both the systole and diastole. The signal processor 5 also creates a graphic interpretation of the pressure signal and parameters, then controls the last major component, the display 6.

The display includes a video screen 7 and a printer 8.

More specifically, the sensor and signal conditioning unit 2 comprises, in connection with the probe 3 a pressure transducer 9 such as a strain gage bridge connected to the input of a differential signal amplifier 10. The output of the amplifier is fed to an analog-to-digital converter 11 which produces a corresponding binary-coded signal. These circuits are energized by a power supply 12.

Typically, a strain gage pressure transducer with a resolution of 2.5 millimeters of mercury and a linearity of one percent of full scale; a differential amplifier with corresponding resolution and linearity; and a eight-bit analog-to-digital converter with a twenty microsecond conversion time, are suggested.

The signal processor 5 comprises a general purpose programmable eight-bit microprocessor 13 equipped with sixty-four kilobytes of random-access memory (RAM) 14, and a read-only memory (ROM) 14a holding a standard operating software and common programming language interpreter or compiler.

The signal processor 5 also comprises a standard user input-output interface 15, a keyboard input interface 16, a video screen output interface 17 and a serial input-output port 18.

A keyboard 19 and disk-drive 20 complete the list of basic components of the system. The disk-drive 20 is used to read the application program recorded on diskettes, as well as some reference parameters. The disk-drive can also be used to record in digital form the information sent to the display unit 6. Alternately, the application program could be stored permanently in a section of the ROM 14a.

The operation of the signal processor 5 in the analysis of the digitized pressure measurement data supplied by the sensor and signal-conditioning unit will be described in detail with reference to FIG. 2 and 3.

Figure 2:
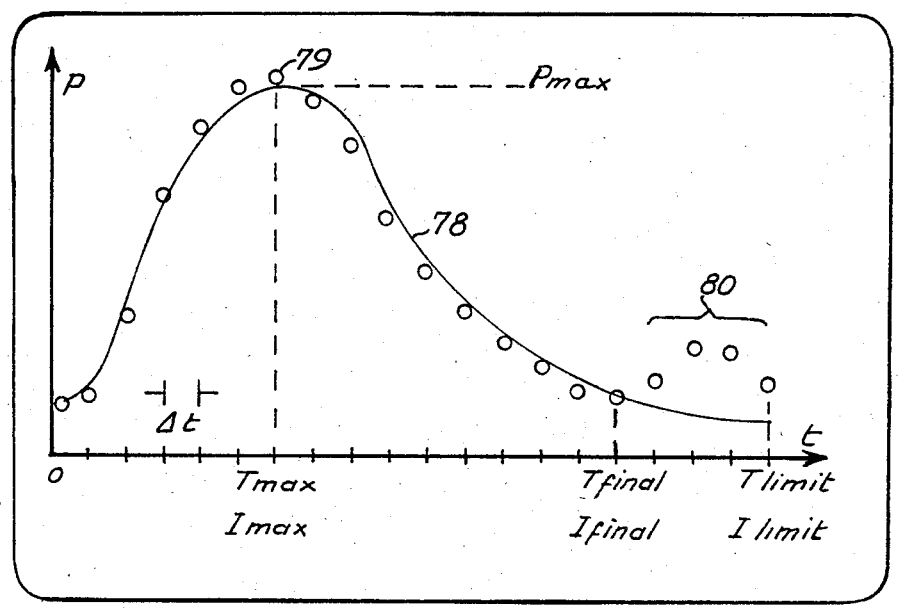
FIG. 2 is a graph of the intra-ventricular or arterial pressure measurements in function of time.

The graph of FIG. 2 illustrates the blood pressure variation during the systolic and diastolic phases of the heart cycle. The full curve 78 represents the theoretical function:

Pressure$=(P)=Bt^y e^{-xt}$ for a particular individual based on accepted norms for his age and sex group.

The dotted line 79 represents the actual measurement samples taken by the apparatus. The rising transient 80 at the bottom of the curve is due to the opening of the mitral valve and/or valvular interaction and aortic recoil.

B represents a factor characteristic of the size of the particular organ under observation. As previously explained, the two parameters y and x denote the particular characteristics of the contraction phenomenon.

Although, ideally, the actual intra-ventricular pressure-time record taken by means of a cardiac catheter would be preferable in order to ascertain the status of the heart muscle,sufficiently accurate diagnosis can be obtained by examination of pressure-time records obtained from the radial, femoral or other arterial locations (as shown in FIG. 1). This is because the parameters (y,x) are temporal in character and as such not greatly affected by amplitude attenuations occurring through the aortic tree. Relative measurements rather than absolute measurements are thus adequate in most cases. The parameters, however, should be weighted or cataloged according to the probing site for a given pathology. In a case of arterio-sclerosis for instance, the value of the parameters measured on the radial artery may vary from those measured at the femoral artery.

Figure 3A:
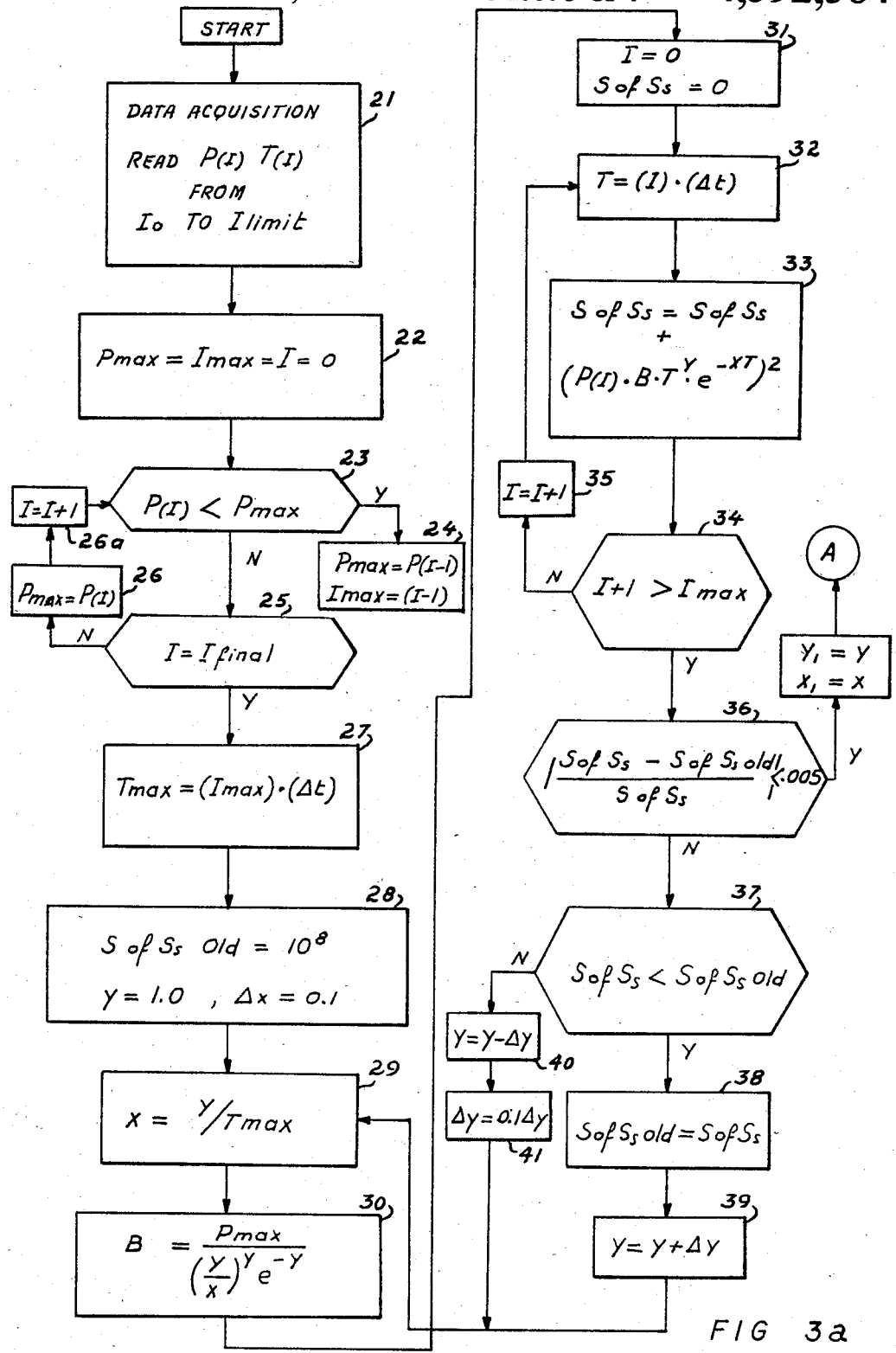
FIGS. 3 and 3b give the flow diagram of the application computer program controlling the operation of the apparatus.
Figure 3B:
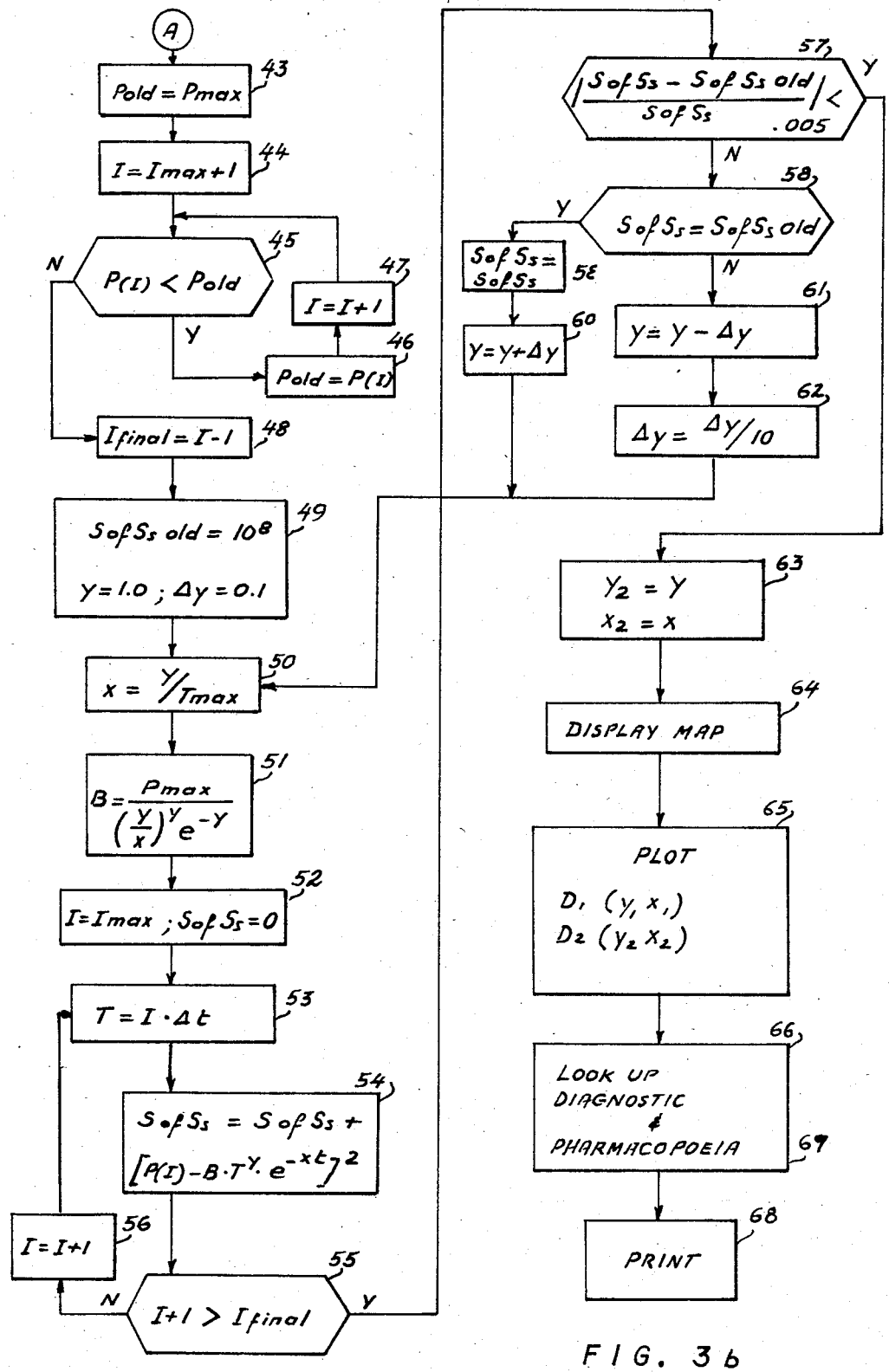

The data obtained by means of the probe 3 and the sensor and signal conditioning unit 2 shown in FIG. 1 are acquired and analyzed by the signal processor 5 in accordance with the flow diagram of FIG. 3a and 3b.

The data acquisition phase 21–27 is done in a series of samplings whose sequence and number are determined by the index I.

As successive readings of the pressure P and time t are taken, the apparatus searches for a drop in the pressure 23, indicating that the maximum pressure Pmax has been reached. The peak pressure is noted 24, as well as the corresponding time Tmax 27, by multiplying the number of samplings taken Imax by the sample period.

The apparatus then seeks to determine the y and x parameters of the theoretical function curve which most closely fits the acquired data, using an iterative sum of squares approximation method.

The program sets an initial trial value 28 for old sum of squares ($10^8$) and parameter y (1.0) and $\Delta y$ (0.1). These values are then used for the computation 29, 30 of parameter x and factor B according to the equations:

$$x = y/T\text{max}; B = P\text{max}/\left(\frac{y}{x}\right)^y e^{-y}$$

The data point index I is then initialized 31 for sum squares equal to zero. Then the sum squares of differences between the sampled and theoretical pressures are computed 32–41 in iterative form until the detection 36 of changes in value of less than 0.005 indicates a converged value of y. At that point, the systolic values y, and x, of the parameters are noted 42.

During this process the value of sum squares is tested 37 to assure that it continues to decrease as y is increased 39. If, instead, the sum square increases, then y is reduced 40,41; and a smaller y increment is used succesivley if necessary, until the converged value of y is achieved.

The analysis of the diastolic phase samplings now begins with the initialization 43–44 of the index.

The samples are taken until the detection of the valve transient 80 which appears near the bottom end of the diastolic drop. The iterative search 45–48 for the transient continues so long as the pressure drops 45.

The curve fitting steps 49–63 mirror those 28–42 used during the systolic phase, with the difference that the index I goes from Imax at peak pressure to Ifinal when the valve transient is detected; instead of from IO to Imax as in the first phase.

A second set of parameters $y_2$, and $x_2$ are then noted for the diastolic phase.

The theoretical pressure curve and the sample measurements shown in FIG. 1 may be displayed on the video screen and 7 and or the printer screen 8 as the data is being acquired.

A trained operator may, upon simple observation of these graphs, draw various conclusions as to the condition of the organ under observation.

The diagnosis phase of the program 64-68, however, provides a more powerful tool for the systematic interpretation of the parameters, leading to a direct formulation of diagnostic and therapeutic indications fetched from pre-recorded data based on accumulated experience.

Figure 4:
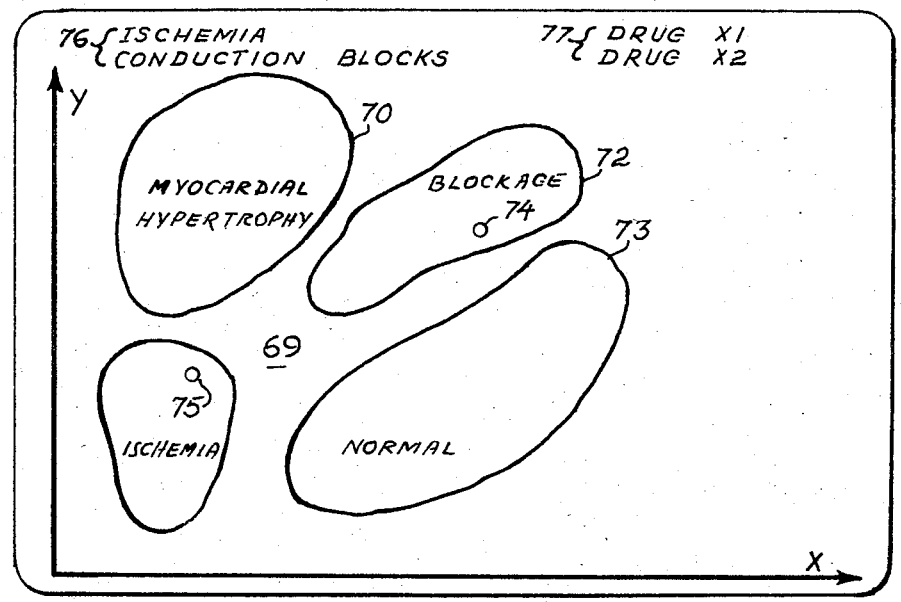
FIG. 4 is illustrating a diagnosing display of the contracting delay and inotropic parameters.

FIG. 4 illustrates the type of displayed or printed information which the apparatus can generate based upon the respective values of y and x.

The final diagnostic phase begins with the display of a map 69 generated from data pre-stored either in the ROM 14a or read by the disk-drive 20.

The map appears on the drawing as the background of FIG. 4. Various zones delineate the area indicative of various pathologies such as myocardial hypertrophy 70, ischemia 71, conduction blocks 72 etc. A normalized zone 73 corresponds to the parameter values of an healthy individual in the patient's age and sex group.

These various zones would be displayed as functions of the actual set of parameters being interpreted, the diagnosis goals as well as the patient's vital statistics. These various criteria can be entered according to well-known routines via the keyboard 19.

Next one or more indicators 74–75 are placed 65 on the map 67 by coupling any two parameters $y_1$, $x_1$, $Y_2$, $x_2$ and ploting one against the other within each pair.

Pathological conditions are pointed out as the indicators 74–75 appears to fall within the respective zones. The location and size of each zone may change as clinical experience accumulates in the diagnosis of various heart conditions.

It should be understood that the territory of each zone 70–73 is predicated upon the predetermined interpretation of each pair of parameters. The location and size of each zone may change as various indicators are displayed.

The coordinates of each indicator are then used to direct the system 66–67 to a stored look-up table, from which printable diagnostic messages 76 or pharmacopoeia 77 may be extracted and printed 68.

It should be understood that the diagnostic process is not limited to the illustrative examples discussed above. Various other combinations and subcombinations of parameters and other factors particular to the patient may be used to address other types of prestored diagnostic and therapeutic indications. For instance, the attenuation of the valve transient 80 detected at an arterial location would indicate the presence of an aneurism in the arterial path. A sharpening of the transient, on the other hand, would reflect the conductive rigidity caused by arterio-sclerosis. The apparatus, thus implemented constitutes a powerful tool in the hands of scientists for further exploration of the cardiac muscle behaviour and the refinement of the diagnostic interpretations of the suggested parameters. As more knowledge is acquired through clinical use of the apparatus on live individuals, as well as applications to in-vitro studies of the cardiac tissues, the practice of this invention may lead to simple and very reliable early diagnosis of pathologies which have been impossible to detect in their early manifestations.

The various hardware components of the apparatus may be selected from commercially available units. The system operating program, data input and output routine and user language assemblers do not differ from standard well-known processes. The implementation of the application programs in accordance with the instant disclosure is well within the ordinary skill of those knowledgeable in the arts of data processing.

The illustrative embodiment described above could be modified and improved, and other related apparatuses may be devised according to the invention and within the scope of the appended claims.

What is claimed is:

1. An apparatus for analysing the biomechanical behaviour of a subject's cardiac muscle and for diagnosing its pathological conditions which comprises:
   pressure sensitive means shaped and dimensioned to monitor the variation of blood pressure in one part of the subject's cardio-vascular system, and for generating electrical signals proportional to said blood pressure;
   means responsive to said electrical signals for recording a plurality of values corresponding to successive blood pressure measurements during at least one cycle of the subject's systolic or diastolic pressure phase in relation to time;
   electrical means for analysing said values and for mathematically deriving at least one critical parameter from the shape of the curve representing the plotting of said values versus time during said cycle and for interpreting said curve as a theoretical pressure-function (P) varying in time (t) with changes of ventricular volume (V) according to the phenomenological model equation:

$$P(V,t) = B(V) t^y e^{-xt}$$

wherein B is a factor corresponding to the influence of the cardiac muscle size, y represents a first parameter, indicative of the excitation-contraction delay, and x represents the second parameter indicative of the inotropic characteristic of the muscle; and means for computing the x and y parameters which most closely fit the curve.

2. The apparatus claimed in claim 1 which further comprises means for plotting one of said parameters against the other.

3. The apparatus claimed in claim 2 wherein said means for plotting comprises means for forming a map having zones corresponding to various pathological cardiac muscle conditions; and means for placing at least one mark of said map, said mark having coordinates corresponding to the computed values of said parameters.

4. The apparatus claimed in claim 2 which further comprises:
   means for storing a plurality of diagnosis messages;
   means for addressing at least one location in said means for storing as a function of said first and second parameters; and
   means for displaying the diagnostic message stored at said location.

5. The apparatus claimed in claim 1 wherein said means for interpreting comprise means for computing a first set of values for said parameters corresponding to the signal recorded during the systolic phase, and a second set of values of said parameters corresponding to signals recorded during the diastolic phase.

6. A method for analysing the biomechanical behaviour of a subject's cardiac muscle and for diagnosing its pathological conditions which comprises:
   measuring by means of at least one pressure sensor the variation of blood pressure in at least one part of the subject's cardio-vascular system during at least one cycle of systolic or diastolic pressure;
   recording a plurality of values corresponding to successive blood pressure measurements taken during said cycle;
   plotting said value in relation to time;

mathematically analysing said plotted values and deriving at least one parameter from the shape of the curve representing the variation of said signals during said cycle; interpreting said curve as a theoretical pressure-function (P) varying in time (t) with changes of ventricular volume (V) according to the phenomenological model equation:

$$P(V,t) = B(V)t^y e^{-xt}$$

wherein B is a factor corresponding to the influence of the cardiac muscle size, y represents a first parameter indicative of the excitation-contraction delay, and x represents a second parameter indicative of the inotropic characteristic of the muscle; and computing the x and y parameters which most closely fit the curve.

7. The method claimed in claim 6 wherein said step of interpreting comprises means for computing a first set of measurements for said parameters corresponding to the signal recorded during the systolic phase, and a second set of measurements for said parameters corresponding to the signal recorded during the diastolic phase.

8. The method claimed in claim 7 which further comprises plotting one of said parameters against the other.

9. The method claimed in claim 8 wherein the step of plotting comprises forming a diagnostic map having the scaled measurements of each of said parameters as respective vertical and horizontal coordinates.

10. The method claimed in claim 9 which further comprises delineating in said map various zones corresponding to pathological muscle conditions; and placing on said map at least one mark having for coordinates the calculated measurements of said parameters.

11. The method claimed in claim 8 which further comprises:

storing a plurality of diagnosis messages;

addressing at least one of said stored messages in function of said first and second parameters; and displaying said message.

12. The method claimed in claim 6 which comprises comparing the measurements of the x and y parameters derived from blood pressure measurements taken from different parts of the subject's cardio-vascular system.

* * * * *